United States Patent [19]

Aboczsky

[11] Patent Number: 5,037,424
[45] Date of Patent: Aug. 6, 1991

[54] INSTRUMENT FOR ORIENTING, INSERTING AND IMPACTING AN ACETABULAR CUP PROSTHESIS

[76] Inventor: Robert I. Aboczsky, 323 E. Saddle River Rd., Upper Saddle River Rd., N.J. 07458

[21] Appl. No.: 609,644

[22] Filed: Nov. 6, 1990

Related U.S. Application Data

[63] Continuation-in-part of Ser. No. 454,432, Dec. 21, 1989, Pat. No. 4,994,064.

[51] Int. Cl.⁵ .............................................. A61F 5/04
[52] U.S. Cl. ..................................................... 606/91
[58] Field of Search ....................... 606/86, 90, 91, 99, 606/100; 623/18, 22

[56] References Cited

U.S. PATENT DOCUMENTS

| | | | |
|---|---|---|---|
| 3,859,992 | 1/1975 | Amstutz | 606/91 |
| 4,100,626 | 7/1978 | White | 606/86 X |
| 4,305,394 | 12/1981 | Bertuch, Jr. | 606/91 |
| 4,457,306 | 7/1984 | Borzone | 606/86 X |
| 4,475,509 | 10/1984 | Oh | 606/91 |
| 4,632,111 | 12/1986 | Roche | 606/53 |
| 4,662,891 | 5/1987 | Noiles | 606/91 X |
| 4,716,894 | 1/1988 | Lazzeri et al. | 606/91 |
| 4,994,064 | 2/1991 | Aboczky | 606/91 |

Primary Examiner—Robert A. Hafer
Assistant Examiner—Sam Rimell
Attorney, Agent, or Firm—Anthony F. Cuoco

[57] ABSTRACT

An instrument for implanting an acetabular cup prosthesis in a patient's acetabulum. The cup is gripped on the base of the instrument and is aligned and inserted in accordance with a plane normal to the plane in which a patient is positioned and normal to a line between the right and left anterior/superior iliac spines. With the acetabular cup so aligned, the cup is impacted to be retained in a prepared acetabulum. The instrument is actuated for gripping the cup and is locked to maintain the cup gripped for the aforenoted alignment, insertion and impaction, and is thereafter unlocked and actuated for releasing the cup so that the instrument can be removed from the cup without disturbing the position thereof. The alignment of the cup is adjustable to accommodatae various implantation situations as may occur.

18 Claims, 2 Drawing Sheets

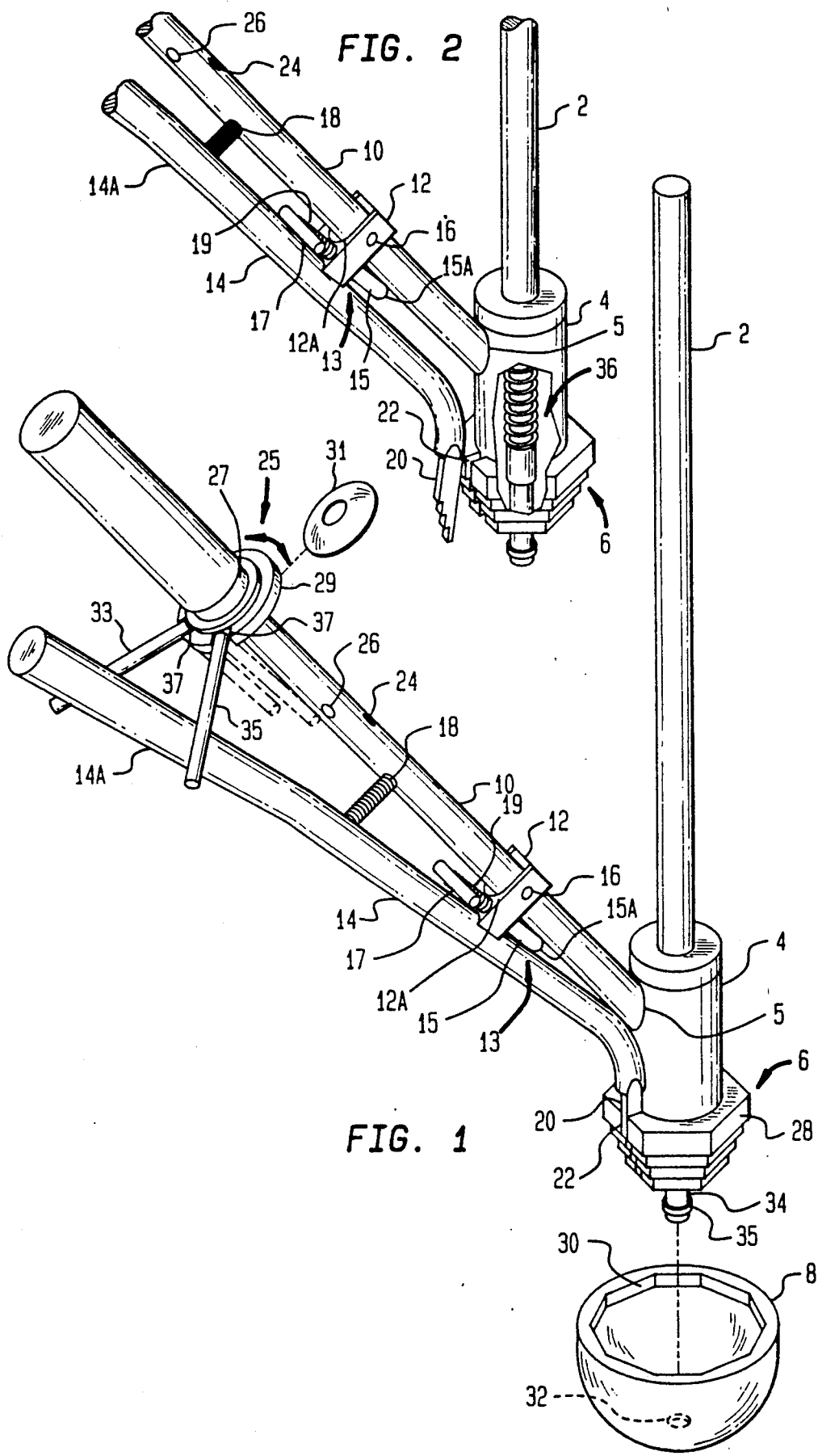

INSTRUMENT FOR ORIENTING, INSERTING AND IMPACTING AN ACETABULAR CUP PROSTHESIS

CROSS REFERENCE TO RELATED APPLICATION

This application is a continuation-in-part of copending U.S. application Ser. No. 454,432 filed by the present inventor on Dec. 21, 1989.

BACKGROUND OF THE INVENTION

A total hip replacement procedure has been developed by Howmedica Division of Pfizer Hospital Products, Inc., Rutherford, N.J. and is described in a monograph entitled *The P.C.A. Primary Hip System Surgical Technique* prepared and published by Pfizer Hospital Products, Inc. in 1988. Howmedica and P.C.A. are registered trademarks of Pfizer Hospital Products, Inc.

The described surgical technique includes implanting an acetabular outer shell or cup prosthesis after appropriately preparing the acetabulum for the implantation. The actual implantation includes orienting, inserting and impacting the acetabular cup in the acetabulum.

Prior to the present invention, a variety of separate instruments have been required to accomplish the implantation. This has been found to be disadvantageous, particularly in view of the time and inconvenience required in switching from one instrument to another, which prolongs the overall operative time. In this connection it will be noted that a major problem encountered in performing surgical procedures such as herein referred to is the risk of infection of the operative area. This risk increases as the operative time increases, and hence it is most desirable to shorten the operative time to the greatest extent possible. Moreover, due to the nature of the procedure, it is imperative that it be performed under circumstances most auspicious to the patient and to the surgeon.

The invention disclosed in the aforementioned copending U.S. application Ser. No. 454,432 overcomes the aforenoted disadvantages and simplifies the implantation, in that only one instrument is required for all of the segments of the procedure. With the instrument therein described, an estimated fifteen to twenty minutes of operative time is saved, which is desirable for the reasons aforenoted.

The invention herein disclosed is an improvement over that disclosed in the referenced co-pending U.S. Application in that a locking arrangement is provided for the several operative members of the instrument thereby facilitating the use thereof, and a more versatile acetabular cup alignment arrangement is provided to accommodate a variety of implantation situations as may from time to time occur.

Accordingly, it is the object of the present invention to provide a single instrument for orienting, inserting and impacting an acetabular cup in a prepared acetabulum as part of a total hip replacement procedure, wherein the use of the instrument is facilitated and the instrument accommodates a wider variety of implantation situations than has heretofore been the case.

SUMMARY OF THE INVENTION

This invention contemplates an instrument for orienting, inserting and impacting an acetabular cup prosthesis for implanting said prosthesis. The instrument includes an impact rod having a base with a shaped end. A coupling rod is affixed to the base of the impact rod and extends angularly therefrom. The coupling rod supports a spring biased pivoting rod having a shaped end which is pivotable away from and toward the shaped end of the impact rod. The shaped end of the impact rod has a slot and the pivoting rod is normally spring biased so that the end thereof is received in the slot, whereby the shaped ends of the impact and pivoting rods cooperatively mate for supporting the acetabular cup. When the pivoting rod is pivoted away from the impact rod, the spring compresses and the shaped end of the pivoting rod is displaced out of the slot to grip the cup in a retaining relationship, whereupon the cup is oriented and inserted in the acetabulum. A locking device is arranged with the coupling and pivoting rods, whereby the pivoting rod is maintained out of the slot to grip the cup without the need for squeezing said rods as would otherwise be the case. The coupling rod carries a rotatably displaceable alignment arrangement which is used to adjustably align the acetabular cup to accommodate a variety of implantation situations.

In using the instrument, the coupling rod is disposed normal to the plane in which a patient is supported. The alignment arrangement includes a bar which is rotatably adjustable about the axis of the coupling rod and which is aligned normal to a line which crosses from the patient's posterior superior iliac spine to the anterior superior iliac spine, whereby the cup, gripped as aforenoted by the locked instrument, is oriented for insertion into the acetabulum.

Upon the cup being so oriented and inserted, the impact rod is impacted, whereby the cup is seated in the acetabulum either by way of a press fit or by cementing. Upon the cup being seated, the instrument is unlocked and the pivoting rod is pivoted against the bias of the spring, whereby the shaped end of the pivoting rod is disposed in the slot in the shaped end of the impact rod for releasing the instrument from the cup. The instrument is thereupon removed from the cup without disturbing its seating.

BRIEF DESCRIPTION OF THE DRAWINGS

FIG. 1 is an exploded perspective representation showing the instrument of the invention and an acetabular cup which is retained thereby for being oriented, inserted and impacted into the acetabulum of a patient, and further showing locking and alignment arrangements according to the invention.

FIG. 2 is a fragmentary partially cut away perspective representation showing a particular feature of the invention wherein the base and end of the impact rod are adapted via a biasing spring arrangement for receiving acetabular cups, and further showing the locking arrangement of the invention.

DETAILED DESCRIPTION OF THE INVENTION

Figure 3:
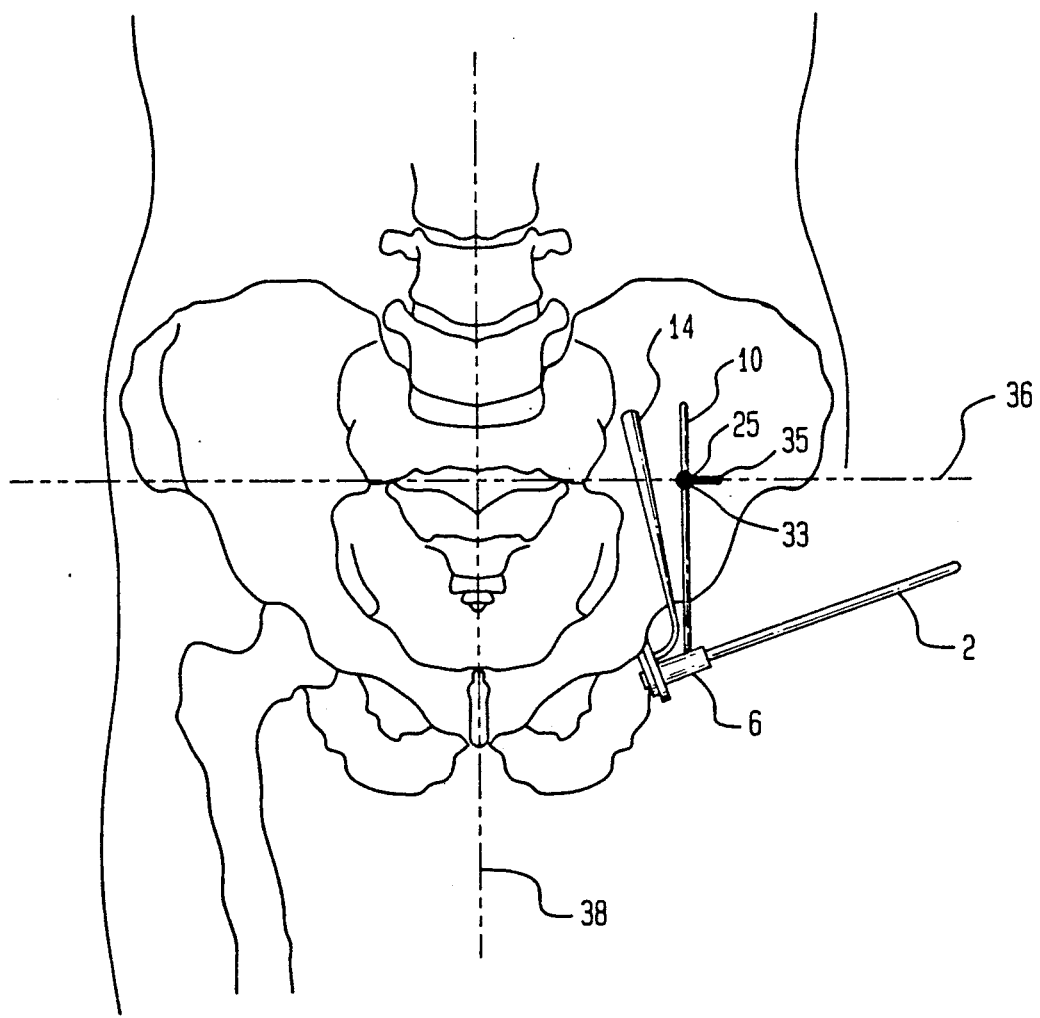
FIG. 3 is a diagrammatic representation showing a line between the right and left anterior/superior iliac spines, and which line is used for aligning the instrument of the invention via the alignment arrangement shown in FIG. 1.

With reference to FIGS. 1 and 2, an impact rod is designated by the numeral 2. Impact rod 2 has a base 4 integral therewith and base 4 has an end 6 integral therewith and shaped in a plurality of step-like gradations 28 for supporting an acetabular cup 8 in a manner which will be hereinafter described.

A coupling rod 10 is affixed to base 4 of impact rod 2 as by welding or the like at 5 and extends angularly therefrom. A clevis-like member 12 is formed integral with a pivoting rod 14. Pivoting rod 14 extends first at a relatively small angle from coupling rod 10 and then at a larger angle to form a handle or gripping portion 14A of rod 14. Coupling rod 10 is supported in the open portion of clevis-like member 12 and is secured therein via a pin 16.

A spring 18 is disposed so as to be captured between coupling rod 10 and pivoting rod 14 above clevis 12. Pivoting rod 14 is normally biased by spring 18 so that a shaped end 20 thereof extends substantially parallel to impact rod 2 and is disposed in a slot 22 in shaped end 6 of impact rod 2. When rod 14 is pivoted about pin 16 toward rod 2 as by squeezing rod 10 and rod 14 at handle portion 14A, spring 18 is compressed and end 20 of rod 14 is displaced from slot 22 as shown in FIG. 2. Thus, when end 20 of pivoting rod 14 is disposed in slot 22, end 6 is adapted for supporting acetabular cup 8 on an appropriate continuous step-like gradation. When end 20 is displaced out of the slot the cup is gripped by end 20 for retaining the cup so supported.

With the arrangement just described rods 10 and 14 must be continuously squeezed to maintain cup 8 gripped. This can be cumbersome for the user since one of the user's hands is continuously occupied for that purpose. The locking arrangement to be next discussed overcomes this disadvantage.

Thus, clevis-like member 12 carries a spring biased locking device designated generally by the numeral 13 and including a rod shaped wedge member 15 having a curved end 15A and a handle 17, and a biasing spring 19 surrounding the upper portion of wedge member 15. Spring 19 is captured between handle 17 and the upper surface 12A of clevis 12.

When cup 8 is positioned as aforenoted, device 13 is actuated by depressing handle 17 against spring 19, whereby wedge member 15 is displaced downwardly in the relatively small angular space between rods 10 and 14 just enough to displace end 20 away from slot 22 to grip cup 8, and to maintain end 20 so displaced, whereupon wedge 15 is captured between rods 10 and 14.

Thus, the hand of the user otherwise required to squeeze rods 10 and 14 to maintain cup 8 gripped is no longer required for that purpose. Indeed, cup 8 can be pre-gripped and locked so gripped as by a nurse or surgical assistant or the like, whereupon both of the user surgeon's hands are free to implant cup 8, as will be hereinafter described.

When cup 8 has been satisfactorily implanted, rods 10 and 14 are squeezed for further displacing end 20 away from slot 22, whereupon wedge 15 is released from between rods 10 and 14 and is upwardly displaced via the biasing action of spring 19. Rods 10 and 14 are released and end 20 is disposed in slot 22 via the biasing action of spring 18, whereupon the instrument is easily removed from implanted cup 8.

It will be understood that rods 2, 10 and 14 are in the same plane. With continued reference to FIG. 1, rod 10 carries a through hole 24 and another through hole 26, said holes being longitudinally displaced from each other above spring 18. The axis of one of the holes 24 and 26 is displaced by approximately thirty-five degrees in one direction from the common plane of rods 2, 10 and 14 and the axis of the other of the holes 24 and 26 is displaced approximately thirty-five degrees in another direction from the common plane of the rods. As described in the aforenoted co-pending U.S. application Ser. No. 454,432, said description being incorporated herein by reference, one of the holes 24 and 26, depending on whether the procedure is being applied to the patient's right or left side, carries a removable alignment bar (not otherwise shown herein) which will be hereinafter described for purposes of comparison with the alignment arrangement of the present invention.

While the removable alignment bar arrangement suffices for most implantation situations, a situation can exist, depending on, among other things, the manner in which a particular patient must be oriented for properly implementing the implantation procedure, which requires an alignment flexibility not thereby available. The flexibility is provided by an adjustable alignment arrangement designated generally by the numeral 25 in FIGS. 1 and 3.

Thus, and with particular reference to FIG. 1, rod 10 includes a reduced diameter portion 27 near the top thereof. A turret member 29 is disposed on reduced diameter portion 27 so as to rest on a spring washer 31 seated at the bottom of the reduced diameter portion. Spring washer 31 may be the commercially available Belleville washer which is well known in the art.

Turret 29 supports a pair of alignment bars 33 and 35 which are fixedly spaced apart at an angle of seventy-two degrees. Bars 33 and 35 are pivotally supported on turret 29 via pivot pin means or the like 37 for being displaceable upwardly and downwardly therefrom so as to be out of the way when not in use. For purposes of illustration, bars 33 and 35 are shown in dotted lines as being downwardly displaced for the reason aforenoted.

The arrangement is such that turret 29 resting on spring washer 31 is rotatably displaceable about the axis of rod 10 in clockwise and counterclockwise directions as shown by the arrow for purposes of aligning the instrument as will be hereinafter described.

With reference to FIGS. 1 and 2, it will be seen that end 6 of impact rod 2 is formed in step-like gradations 28 as aforenoted, with four such gradations being shown for purposes of illustration. The smallest gradation is at the bottom of end 6 and the largest gradation is at the top thereof. Each of the gradations 28 is shaped in a polygonal configuration, with a hexagon being shown for purposes of illustration.

Each of the step-like gradations 28 is adapted for supporting an acetabular cup 8 of a different size, i.e. diameter and depth. Thus, the smallest acetabular cup 8 fits on the lowermost gradation 28 and the largest acetabular cup fits on the uppermost gradation 28. In this regard, it will be recognized that acetabular cups 8 are substantially semi-spherical in shape and have an internal polygonal mounting rim 30 extending circumferentially therearound. For purposes of illustration, surface 30 is shown shaped as a decagon.

Thus, as will be discerned from FIG. 1, an acetabular cup 8 of a desired size is disposed over end 6, with the appropriate gradation 28 at least partly engaging internal rim 30 of cup 8. With the polygonal configuration of gradations 28 and rim 30 being different as described, the painstaking and time consuming alignment of each of the gradation sides with each of the rim sides is avoided as would not be the case if both polygonal configurations were the same.

Cup 8 is fabricated with a through hole 32 on the bottom thereof as will be recognized by those skilled in the art. While hole 32 is shown as being centrally disposed, some implantations may require the hole to be off center. Indeed, cup 8 may have several such holes in various locations at the bottom thereof to provide a desired flexibility in usage. A pin 34 extends from the lowermost gradation 28 and into hole 32. Pin 34 has a shoulder 35 and is spring biased via a spring arrangement 36 as shown in FIG. 2, whereby the pin is displaceable into and out of end 6 and base 4 as will be discerned from the Figure. The purpose of pin shoulder 35 is to limit the extension of pin 34 into hole 32 to prevent the pin from extending through the hole into the acetabulum. The pin is displaceable against the bias of spring arrangement 36 so that end 6 can receive the largest acetabular cup 8 on the uppermost polygonal gradation 28.

With an acetabular cup 8 so disposed on end 6, cup 8 is gripped and locked gripped as aforenoted.

USE OF THE INVENTION

In using the instrument described and with an acetabular cup 8 gripped and locked gripped as aforenoted, coupling rod 10 is disposed perpendicular to the plane in which the patient is supported, which is a substantially horizontal plane. In the invention described in the aforenoted co-pending U.S. application Ser. No. 454,432, the removable alignment bar heretofore referred to extends through one of the holes 24, 26, as the case may be, and is aligned so as to be normal to a line 36 between the right and left anterior/superior iliac spines normal to the patient's pelvic line 38, with lines 36 and 38 shown in FIG. 3. While this alignment arrangement may suffice for many cases, it is restrictive in that only one position of the alignment bar for each side of the patient is available as will now be understood. The present invention recognizes that situations could well occur where other alignment bar positions are required for properly implementing an implantation procedure. Alignment arrangement 25 provides this flexibility. In this regard, it is noted that, as heretofore described, turret 29 is rotatably displaceable via the arrangement including spring washer 31 so that the position of alignment bars 33 and 35 is adjustable relative to the common plane of rods 2, 10 and 14.

With continued reference to FIG. 3, turret 29 (FIG. 1) is rotated to a desired alignment position as aforenoted. One of the alignment bars 33 or 35 (FIG. 1), depending on whether the procedure is being applied to the patient's right or left side and shown as bar 33 for purposes of illustration, is aligned so as to be normal to line 36.

The flexibility afforded by the alignment arrangement disclosed herein will be readily discernable. The angular distance between the two alignment bars 33 and 35 is fixed and the positioning of a single alignment bar in one or the other of a pair of holes in bar 10 as has been otherwise been the case is eliminated. Further, the position of the particular alignment bar relative to the common plane of rods 2, 10 and 14 which has otherwise been fixed is now adjustable, as is advantageous in accommodating a variety of implantation situations.

With the instrument thus aligned, which accomplishes the proper orientation of acetabular cup 8, the cup is inserted in the previously prepared acetabulum and impact rod 2 is impacted, whereby the cup is seated in the acetabulum. Upon the cup being so seated, locking device 13 is actuated for releasing the grip on the cup, whereby the instrument is removed from the cup without disturbing its seating, as aforenoted.

It will be understood by those skilled in the art that the instrument herein described has a versatility in use in that it may be used for an acetabular cup prosthesis which is either press fitted or cemented into the acetabulum. Significantly, the instrument saves a considerable amount of operative time since it incorporates several different instruments and eliminates the time required in switching from one instrument to the other.

The instrument can be fabricated from stainless steel, chrome steel, cobalt steel or titanium so as to have a height and length and an overall weight acceptable for orthopaedic surgeons, and for meeting the demands of working within a relatively small cavity and having enough maneuvering space as is required.

The design of the instrument is such that it retains the acetabular cup in an ideal position, and holds it firmly so that even within the bony acetabulum, the cup may be maneuvered to obtain ideal alignment. The tool itself has the ability to withstand high temperatures necessary for sterilization processes prior to use. Further, its simplified design renders it easy to learn its usage and to receive wide acceptability by the orthopaedic community. The particular arrangements disclosed for locking the instrument in an acetabular cup gripping mode and for providing adjustable alignment of the cup enhance said usage.

It will be understood that the instrument may be fabricated for accommodating both alignment arrangements herein described, i.e. holes 24 and 25, and turret and angularly spaced bars 35 and 37, whereby the user may select an alignment arrangement most suitable for a particular situation.

Although the invention has been described with reference to an acetabular cup having an internal rim with a particular polygonal configuration such as illustrated in the aforementioned "Howmedica" system, it will be understood that the instrument may be modified to be adaptable to any such system wherein the cup has an internal rim configuration which is circular, square, triangular, or any other shape, the same being within the scope of the invention. Thus, the instrument may be modified for use with the "Richards" system, the "Zimmer" system, the "Protek" system, the "De Puy" system, and all other systems using a press fit or cemented acetabular component.

With the above description of the invention in mind, reference is made to the claims appended hereto for a definition of the scope of the invention.

What is claimed is:

1. An instrument for orienting, inserting and impacting an acetabular cup prosthesis, comprising:
   first, second and third rods disposed in a common plane;
   the first rod having a bottom with a shaped end and a slot in said end;
   the second rod extending angularly from the bottom of the first rod;
   the third rod displaceably coupled to the second rod and having an end receivable in the slot in the end of the first rod and shaped to match the shape thereof;
   a spring captured between the second and third rods and normally biasing the third rod so that the shaped end thereof is received in the slot in the end of the first rod, whereby said first rod end is adapted for supporting an acetabular cup;

means arranged with the second and third rods for displacing the end of the third rod out of the slot to a position for gripping the cup and for locking the end of the third rod in the displaced position;

means arranged with the second rod for adjustably aligning the gripped cup for insertion into a patient's acetabulum;

the second rod being disposed in a plane normal to the plane in which the patient is supported and the adjustable aligning means including a pair of bars, one of which bars, in accordance with the side of the patient receiving the prosthesis, is disposed normal to a line extending between the right and left anterior/superior iliac spines of the patient, whereby the gripped cup is aligned for insertion into the patient's acetabulum, and thereafter inserted therein and impacted via impaction of the first rod to seat the aligned and inserted cup; and the displacing and locking means being unlocked and the third rod displaced by the bias of the spring captured between the second and third rods, whereby the end of the third rod enters the slot to release the grip on the seated acetabular cup, whereupon the instrument is removable from said cup without disturbing its seating.

2. An instrument as described by claim 1, wherein the means arranged with the second and third rods for displacing the end of said third rod out of the slot to a position for gripping the cup and for locking the end of the third rod in the displaced position includes:

wedge means supported between the second and third rods below the spring;

a spring for biasing the wedge means so that said wedge means is normally ineffective for displacing the end of the third rod out of the slot, and said wedge means being downwardly displaced against the bias of the wedge means biasing spring for displacing the end of said third rod against the bias of the spring captured between the second and third rods out of the slot to the displaced position; and the wedge means being thereupon captured between the second and third rods for locking the end of the third rod in said displaced position.

3. An instrument as described by claim 2, wherein the locking means being unlocked includes:

the third rod being displaced against the bias of the spring captured between the second and third rods for displacing the end of the third rod further out of the slot, whereupon the wedge means is released from between the second and third rods; and the third rod displaced by the bias of the spring captured between the second and third rods, whereby the end of the third rod enters the slot to release the grip on the seated acetabular cup.

4. An instrument as described by claim 1, wherein the means arranged with the second rod for adjustably aligning the gripped cup for insertion into a patient's acetabulum includes:

turret means supported by the second rod so as to be rotatable about the axis thereof;

the pair of bars extending from the turret means in fixed angular spaced relationship and rotatable with said turret means so that the axis of each of the pair of bars is in a plane angularly displaced from the common plane of the first, second and third rods, with said angular displacement being adjustable commensurate with the rotation of the turret means.

5. An instrument as described by claim 4, wherein:

the pair of bars extend from the turret means so as to be displaceable upwardly and downwardly relative thereto to be out of the way when not in use.

6. An instrument as described by claim 1, wherein:

the end of the first rod is shaped as a plurality of step-like gradations and the end of the third rod received in the end of the slot in the first rod is shaped in a plurality of matching step-like gradations, whereupon said first rod end is shaped as a plurality of continuous step-like gradations for being adapted to support one of a plurality of acetabular cups on a corresponding one of the continuous step-like gradations.

7. An instrument as described by claim 2, wherein:

the lowermost of the continuous step-like gradations is the smallest in size for supporting a smallest cup and the uppermost of said continuous gradations is the largest in size for supporting a largest cup.

8. An instrument as described by claim 2, wherein: each of the plurality of continuous step-like gradations is polygonal in shape for engaging a polygonal shaped inner surface of the acetabular cup for supporting said cup.

9. An instrument as described by claim 3, including:

a pin extending from within the bottom of the first rod and through the lowermost of the step-like gradations at the end thereof;

the acetabular cups having at least one through hole into which the pin extends when one of said cups is supported on a corresponding one of the continuous step-like gradations; and the pin having a shoulder for limiting the extension of the pin into the cup hole.

10. An instrument as described by claim 5, wherein:

a spring is disposed within the bottom of the first rod and engages the pin in spring biasing relationship so that the pin extends a predetermined distance from the lowermost of the step-like gradations at the end of the bottom of the first rod; and said pin is displaced against the bias of the spring disposed within the bottom of the first rod so that the uppermost of the continuous step-like gradations supports the largest acetabular cup.

11. An instrument as described by claim 1, including:

the end of the third rod being substantially parallel to the first rod;

said third rod having a first section extending from the end thereof at a first angle from the second rod; and said third rod having a second section extending from the first section at a second angle from the second rod, said second angle being greater than the first angle.

12. An instrument as described by claim 7, wherein:

the spring captured between the second and third rods is captured between the second rod and the first portion of the third rod near the end thereof.

13. An instrument as described by claim 8, wherein:

the third rod is displaceably coupled to the second rod between the spring captured between the second rod and the first portion of the third rod and the end of the third rod below said spring.

14. An instrument as described by claim 8, wherein:

the third rod is displaced against the bias of the spring when the second section of the third rod is displaced toward the second rod.

15. An instrument as described by claim 4, wherein:
the polygonal shape of the continuous step-like gradations is different than the polygonal shape of the inner surface of the acetabular cup.

16. An instrument for orienting, inserting and impacting an acetabular cup prosthesis, comprising:
first, second and third rods disposed in a common plane;
the first rod having a bottom with a shaped end and a slot in said end;
the second rod extending angularly from the bottom of the first rod;
the third rod displaceably coupled to the second rod and having an end receivable in the slot in the end of the first rod and shaped to match the shape thereof;
a spring captured between the second and third rods and normally biasing the third rod so that the shaped end thereof is received in the slot in the end of the first rod, whereby said first rod end is adapted for supporting an acetabular cup;
means arranged with the second and third rods for displacing the end of the third rod out of the slot to a position for gripping the cup and for locking the end of the third rod in the displaced position;
a pair of holes extending through the second rod in longitudinal spaced relation, with the axis of one of said holes being in a plane angularly displaced in one direction from the common plane of the first, second and third rods and the axis of the other of said holes being in a plane angularly displaced in another direction from said common plane;
a bar extending through one of said holes in accordance with the side of a patient which is receiving the prosthesis;
the second rod being disposed in a plane normal to the plane in which the patient is supported and the bar being disposed normal to a line extending between the right and left anterior/superior iliac spines of the patient, whereby the gripped cup is aligned for insertion into the patient's acetabulum, and thereafter inserted therein and impacted via impaction of the first rod to seat the aligned and inserted cup; and
the displacing and locking means being unlocked and the third rod displaced by the bias of the spring captured between the second and third rods, whereby the end of the third rod enters the slot to release the grip on the acetabular cup, whereupon the instrument is removable from said cup without disturbing its seating.

17. An instrument as described by claim 16, wherein the means arranged with the second and third rods for displacing the end of said third rod out of the slot to a position for gripping the cup and for locking the end of the third rod in the displaced position includes:
wedge means supported between the second and third rods below the spring;
a spring for biasing the wedge means so that said wedge means is normally ineffective for displacing the end of the third rod out of the slot, and said wedge means being downwardly displaced against the bias of the wedge means biasing spring for displacing the end of said third rod against the bias of the spring captured between the second and third rods out of the slot to the displaced position; and
the wedge means being thereupon captured between the second and third rods for locking the end of the third rod in said displaced position.

18. An instrument as described by claim 17, wherein the locking means being unlocked includes:
the third rod being displaced against the bias of the spring captured between the second and third rods for displacing the end of the third rod further out of the slot, whereupon the wedge means is released from between the second and third rods; and
the third rod displaced by the bias of the spring captured between the second and third rods, whereby the end of the third rod enters the slot to release the grip on the seated acetabular cup.

* * * * *